United States Patent
Mellström et al.

(10) Patent No.: US 6,364,525 B1
(45) Date of Patent: Apr. 2, 2002

(54) X-RAY EXAMINATION APPARATUS WITH A LIFTING AND ROTATING DEVICE FOR AN APPARATUS COMPONENT

(75) Inventors: Erik Mellström, Järfälla; Per Stenfors, Spanga; Jan Narfström, Sollentuna, all of (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/585,535

(22) Filed: Jun. 2, 2000

(30) Foreign Application Priority Data

Jun. 10, 1999 (SE) .............................. 9902181

(51) Int. Cl.7 .............................................. H05G 1/02
(52) U.S. Cl. ..................... 378/197; 378/195; 378/196; 378/209; 74/89.22
(58) Field of Search ................. 378/167, 189, 378/195, 196, 197, 209; 74/89.2, 89.21, 89.22

(56) References Cited

U.S. PATENT DOCUMENTS

| | | | |
|---|---|---|---|
| 4,019,059 A | 4/1977 | Brundin et al. ............ 378/209 |
| 4,220,861 A | 9/1980 | Colombo et al. ...... 250/363.05 |
| 4,481,656 A | 11/1984 | Janssen et al. ............ 378/196 |
| 4,802,198 A * | 1/1989 | Guenther et al. ........... 378/197 |
| 4,912,754 A | 3/1990 | VanSteenburg ............ 378/209 |
| 4,955,046 A | 9/1990 | Siczek et al. ............... 378/197 |
| 5,048,069 A * | 9/1991 | Siczek ......................... 378/197 |
| 5,412,823 A | 5/1995 | Sitta ................................ 5/601 |
| 5,469,492 A * | 11/1995 | Burbury et al. ............. 378/197 |
| 6,070,480 A * | 6/2000 | Kerschner .................... 74/89.2 |
| 6,193,415 B1 * | 2/2001 | Kadowaki et al. .......... 378/198 |

FOREIGN PATENT DOCUMENTS

| | | |
|---|---|---|
| DE | 197 25 457 | 12/1998 |
| WO | WO 89/08211 | 9/1989 |

* cited by examiner

Primary Examiner—Robert H. Kim
Assistant Examiner—Allen C. Ho
(74) Attorney, Agent, or Firm—Schiff Hardin & Waite

(57) ABSTRACT

An x-ray examination apparatus has a base with at least one fixed part and one carriage that can be vertically shifted in relation to the fixed part. The carriage is provided with a horizontally projecting shaft, to which an apparatus component is mounted and which has a center axis around which the apparatus component can rotate. A pulley with a peripheral surface that is at least partially round is rotationally mounted to the shaft and is firmly connected to the apparatus component. A first pair of wheels is arranged at the fixed part of the base and a connector is provided to connect the pulley to the wheels so that whenever the wheels are respectively simultaneously rotated in different directions, the pulley and thus the apparatus component are vertically shifted and whenever the wheels are rotated in the same direction, the pulley and thus the apparatus component are caused to rotate around the center axis.

10 Claims, 5 Drawing Sheets

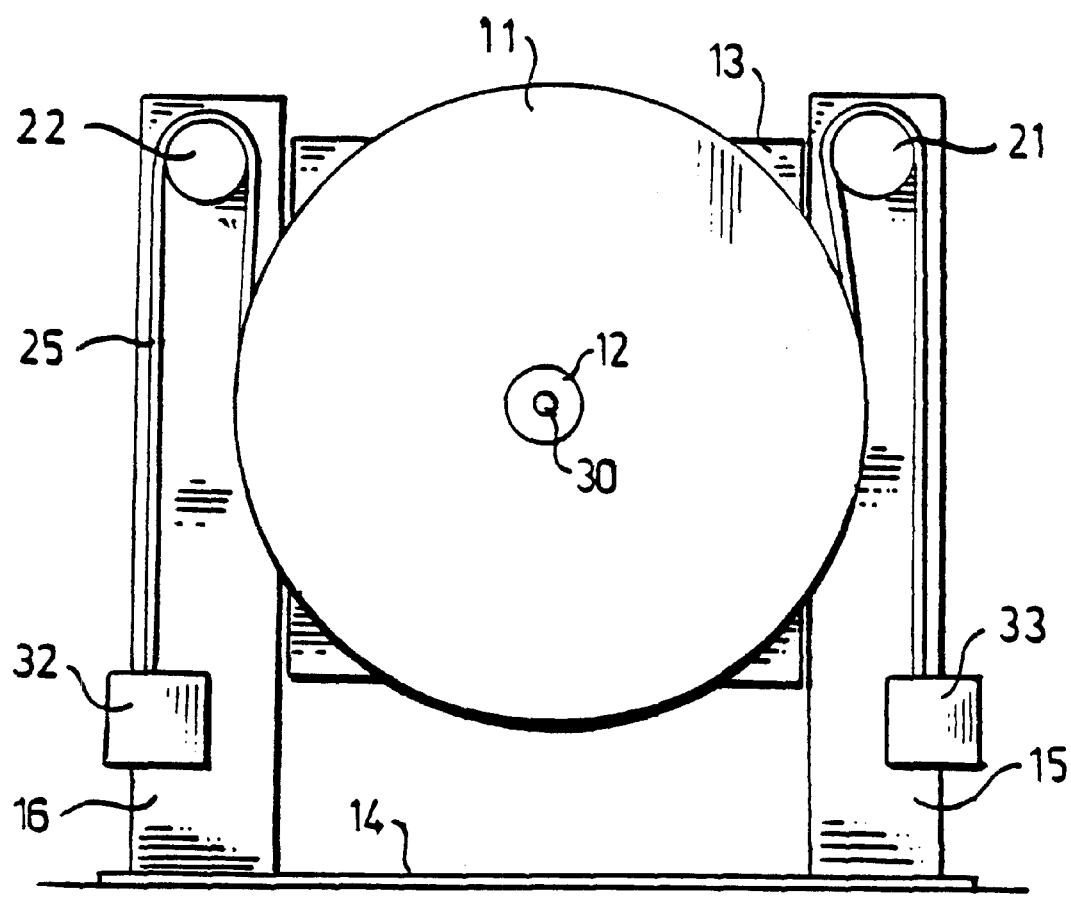

X-RAY EXAMINATION APPARATUS WITH A LIFTING AND ROTATING DEVICE FOR AN APPARATUS COMPONENT

BACKGROUND OF THE INVENTION

1. Field of the Invention

The present invention is directed to an x-ray examination apparatus of the type having a base with at least one fixed part and a carriage that shifts vertically in relation to the fixed part, the carriage having a horizontally projecting shaft to which an apparatus component is connected and around the center axis of which the apparatus component can rotate.

2. Description of the Prior Art

An x-ray examination apparatus of the above type is commercially available from the Siemens company called "Polystar T.O.P". The projecting shaft is provided with a worm drive that is itself firmly connected to the apparatus component via a beam. The apparatus also has a patient table, a C-arm support with an x-ray tube and a radiation detector. The patient table and the C-arm support are attached at the beam and are arranged to be movable independently of one another at this beam. A carriage is arranged at the base, and thus also at the beam, and can be shifted vertically with a threaded screw driven by a motor. The beam can rotate around the center axis of the worm drive by means of the worm drive. Whenever the center of gravity of the apparatus is shifted along the beam in connection with an examination, a worm drive with exact tolerances is required so that only very little play is present between the flights of the worm screw and the teeth of the worm gear. Only then can a stability be attained in the apparatus such that sudden jerks or angle changes of the beam can be avoided. Worm drives of this type are extremely expensive. The threaded screw and the motor for the vertical shifting of the carriage must also be dimensioned such that they can raise and lower the apparatus without difficulty. This design is complex overall and expensive to manufacture.

SUMMARY OF THE INVENTION

An object of the present invention is to provide a lifting and rotating device for an x-ray examination apparatus of the type described above that is relatively inexpensive to manufacture and also maintains the apparatus stable during a shifting of the center of gravity.

This object is achieved in an x-ray examination apparatus having a first lifting and rotating device with a shaft to which a pulley is rotationally mounted that has a peripheral surface, at least a portion of the peripheral surface being round. The pulley is firmly connected to an apparatus component. A pair of wheels is arranged at a fixed part of the base and a connector connects the pulley to the wheels such that whenever the wheels of the pair of wheels are simultaneously turned in different directions, the pulley and thus the apparatus component are shifted in a vertical direction and whenever the wheels of the pair of wheels are turned in the same direction, the shaft and thus the apparatus are rotated around the center axis. As a result, a lifting and rotating device is attained that is relatively simple in construction, and thus inexpensive to manufacture and is substantially stable.

In a further embodiment of the lifting and rotating device according to the invention, a second pair of wheels is arranged at the carriage or at the fixed part of the base, and the connector in sequence encompasses a part of one wheel of the first pair of wheels, and partially encompasses one wheel of the second pair of wheels, and partially encompasses the pulley, and partially encompasses the second wheel of the second pair of wheels and partially encompasses the second wheel of the first pair of wheels. The first pair and the second pair of wheels are arranged at different levels. A further stabilization of the device is achieved by the second pair of wheels and the described path of the connector.

The wheels of the first pair of wheels are driven in accordance with the invention and the wheels of the second pair of wheels are deflection wheels.

The connector is preferably a chain, but alternatively can be a toothed belt.

In another embodiment of the invention, a second lifting and rotating device is arranged parallel to the first lifting and rotating device. This is a safety measure that assures a steady functioning of the device.

DESCRIPTION OF THE DRAWINGS

FIG. 6 schematically illustrates a fourth exemplary embodiment of a lifting and rotating device according to the invention.

DESCRIPTION OF THE PREFERRED EMBODIMENTS

Figure 1:
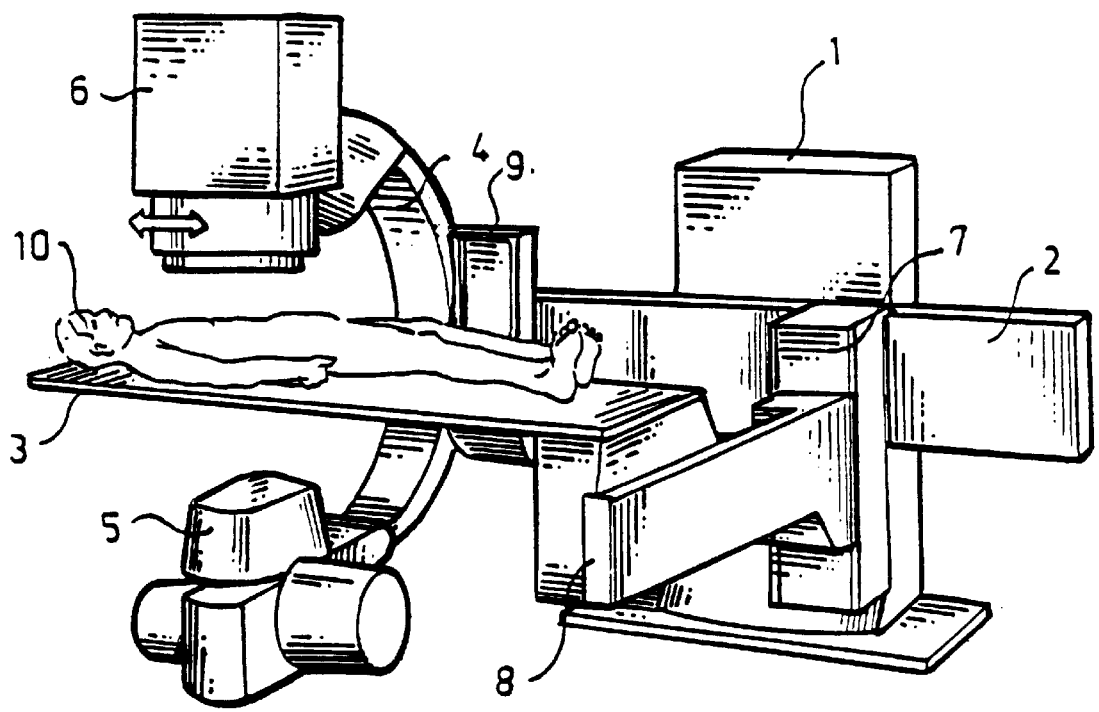
FIG. 1 shows an x-ray examination apparatus with a base in which a lifting and rotating device according to the invention can be mounted.

An x-ray examination apparatus with a base 1 is shown in FIG. 1. The apparatus has a beam 2 mounted at the base 1, and includes x-ray imaging components such as a patient table 3 and a C-arm support 4 with an x-ray tube 5 and a radiation receiver 6. The patient table 3 is connected to the beam 2 via a support 7 and a boom 8. The support 7 and thus also the table 3 are arranged to shift along the beam 2. The C-arm support 4 is also connected to the beam 2 via another support 9 and can be shifted along this support 9. A patient 10 is shown in FIG. 1 on the table 3. The beam 2 and thus the entire apparatus can be shifted in height using a lifting and rotating device and also can be rotated around a shaft which cannot be seen in FIG. 1, but which is described below.

Figure 2:
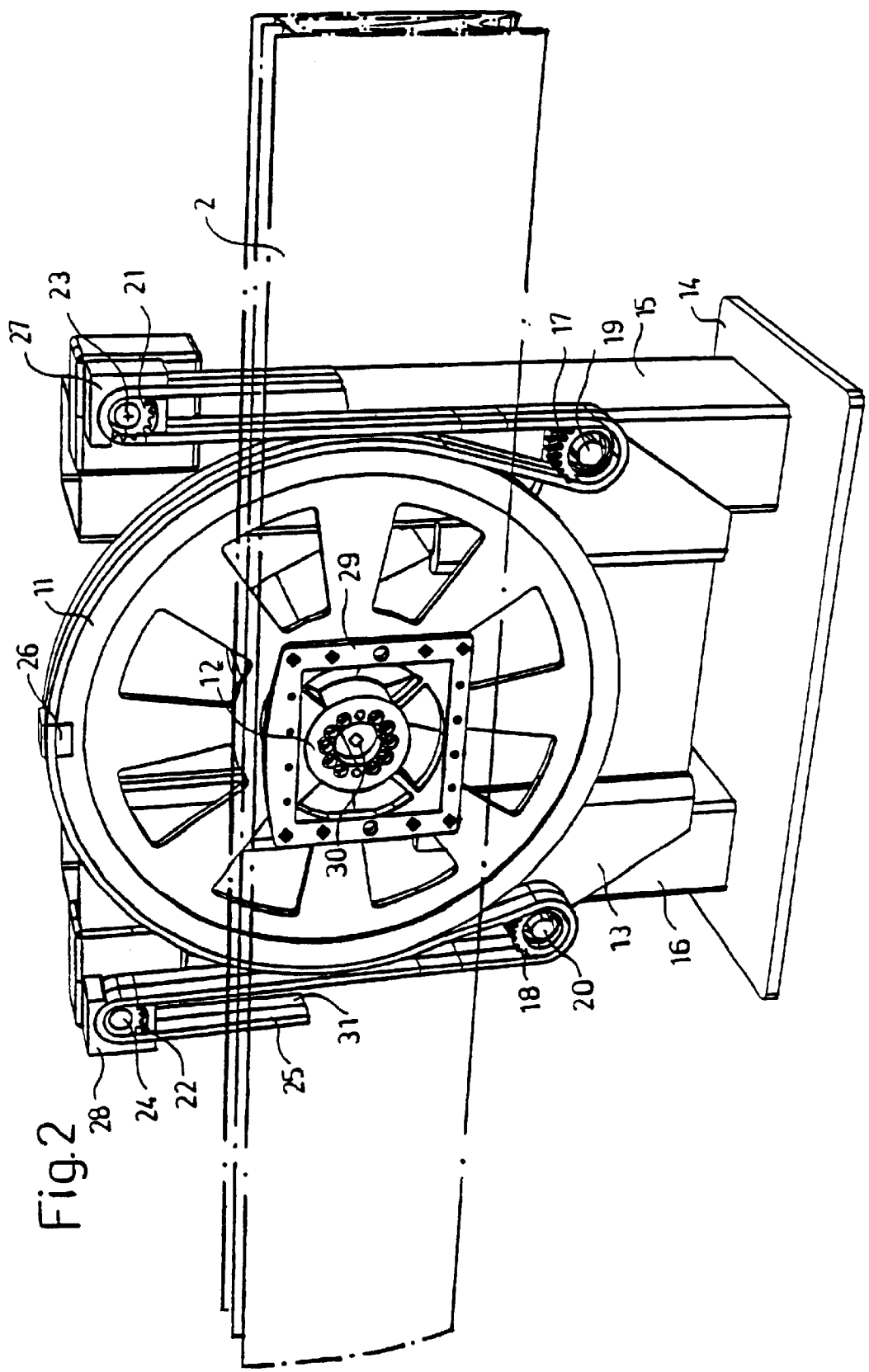
FIG. 2 shows the base according to FIG. 1 without a cover, revealing the inventive lifting and rotating device.

The base 1 is shown without a cover in FIG. 2. As a result, the lifting and rotating device is revealed. The device has a wheel-like pulley 11 that is connected to a carriage 13 via a shaft 12. The carriage 13 can be vertically shifted using known means (therefore not shown in more detail) between two columns 15, 16 firmly arranged in the base plate 14. The device also has a pair of drive wheels 21, 22 that are respectively attached at the columns 15, 16 and are connected to motors (not shown) via respective shafts 23, 24. The device further has a pair of deflection wheels 17, 18 that are attached at the carriage 13 and can rotate around respective shafts 19, 20. A connector in the form of a chain 25 connects the pairs of wheels 17, 18, 21, 22 to the pulley 11. Thus the chain 25 partially encompasses the drive wheel 22 and thereafter partially the deflection wheel 18, thereafter encompasses the pulley 11, thereafter partially encompasses the deflection wheel 17 and finally, the chain 25 partially encompasses the drive wheel 21. FIG. 2 shows that the chain 25 can be firmly connected to the pulley 11 via a bracket 26. Guide shoes 27, 28 assure that the chain 25 is not released from the drive wheels 21,22. The beam 2 that is indicated by dotted lines in FIG. 2 is firmly connected to the pulley 11 via a part 29 provided with a flange.

With the described construction of the lifting and rotating device using the drive wheels 21, 22, the pulley 11, or the beam 2 and thus the apparatus component can be shifted in a vertical direction, and can be rotated separately around the shaft 12 or caused to execute a combined, continuous lifting and rotating motion. Movement in a vertical direction occurs when the drive wheels 21, 22 are caused by the motors to simultaneously rotate in opposite directions. As a result, the deflection wheels 17, 18 and thus the carriage 13 are forced by the chain 25 to be shifted along the columns 15, 16. When the drive wheels 21, 22 are rotated in the same direction, the pulley 11, or the beam and thus the apparatus, are caused by the chain 25 to rotate around the axis 30 of the shaft 12. The motors for the drive wheels 21,22 are preferably parts of a software driven control system that is known and therefore not described in more detail. For a combined lifting and rotating movement of the beam 2, the control system is controlled by the software such that a continuous and smooth movement of the apparatus occurs.

Figure 3:
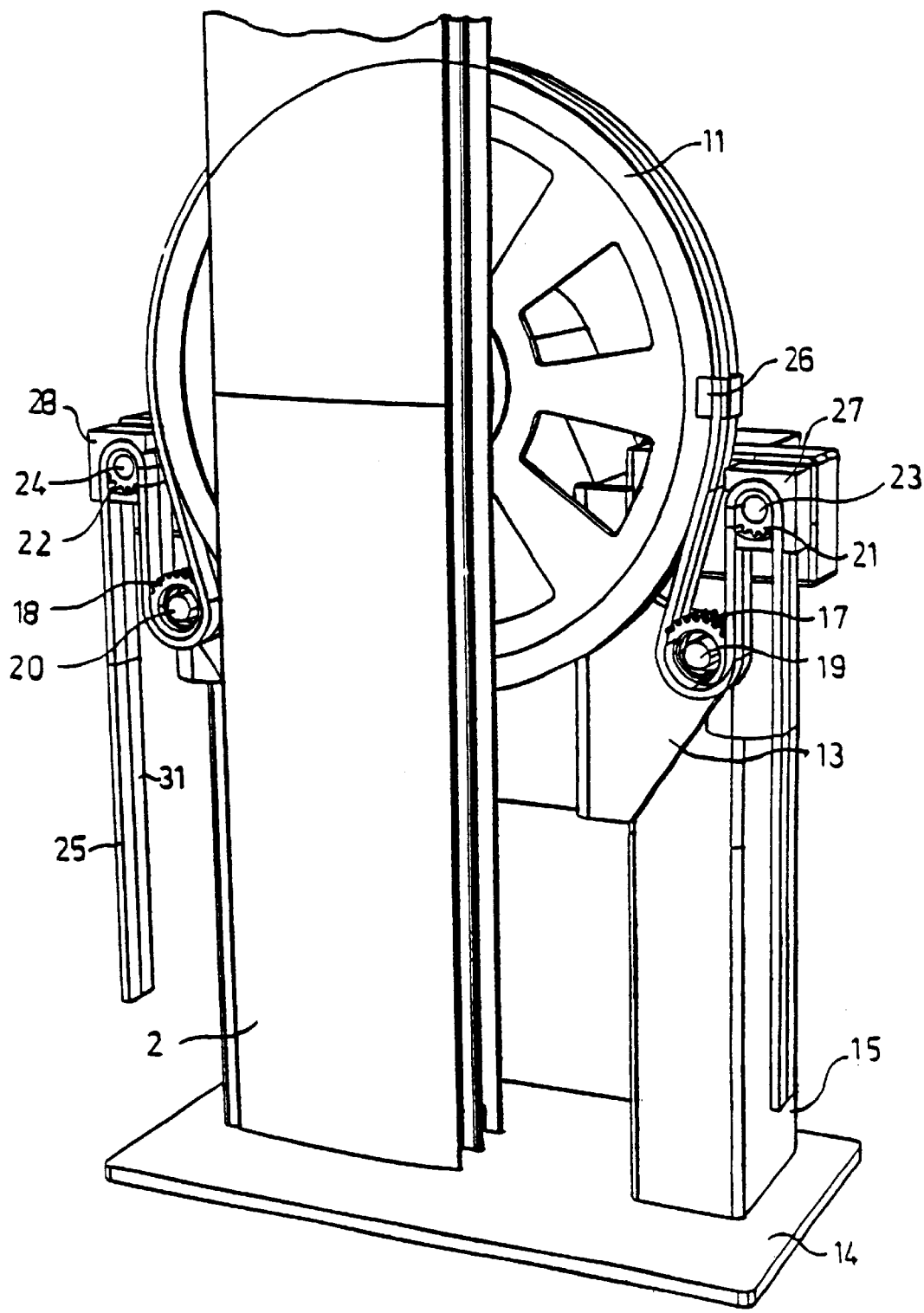
FIG. 3 shows the base according to FIG. 2 with the lifting and rotating device in a different position from that shown in FIG. 2.

A situation is shown in FIG. 3, wherein the pulley 11, or the beam 2, has been alternately lifted and lowered into a position in the described fashion by the drive wheels 21 and 22 as well as the motors of the control system, wherein the beam 2 occupies a vertical position.

FIGS. 1 and 2 show that the drive wheels and deflection wheels 21, 22, 17,18 as well as the pulley 11 exhibit two peripheral surfaces that allow that a further chain 31 can run parallel to the aforementioned chain 25. This further chain 31 serves as a safety measure and as a strengthening of the design.

The pulley 11 exhibits a relatively large diameter. As long as the center of gravity of the apparatus is within the circumference of the pulley 11, a particularly stable lifting and rotating device is achieved. Regulation of the center of gravity can be software-controlled, i.e. a shifting of the patient table 3 and of the C-arm support 4 along the beam 2 such that the center of gravity is located within the circumference of the pulley 11.

Figure 4:
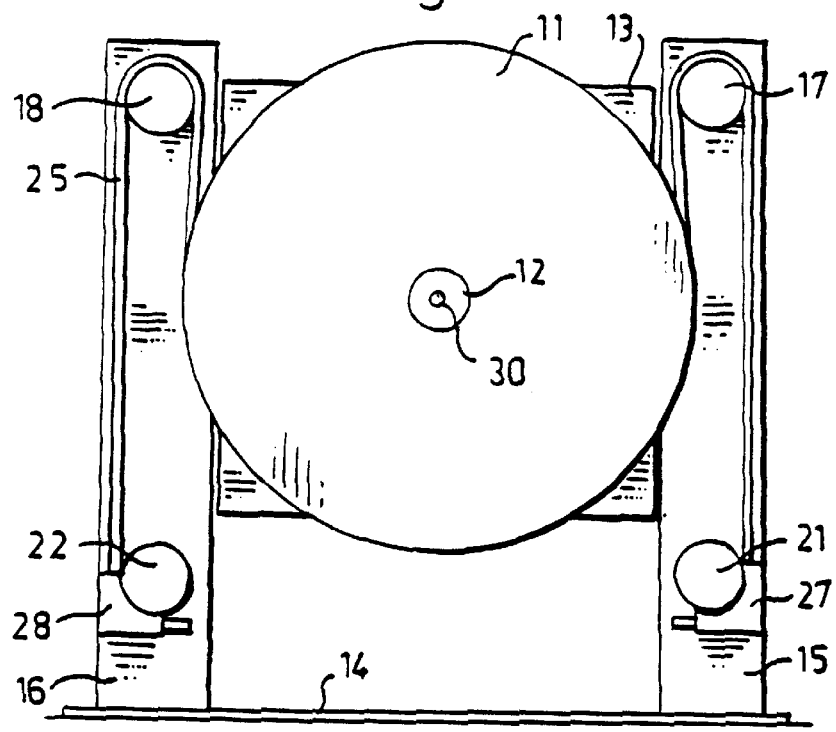
FIG. 4 schematically illustrates a second exemplary embodiment of a lifting and rotating device according to the invention.

A further exemplary embodiment of the lifting and rotating device according to the invention is schematically shown in FIG. 4. The reference characters are the same as in FIGS. 1 and 2. In the embodiment in FIG. 4, both the pair of drive wheels 21, 22 and the pair of deflection wheels 17, 18 are attached at the respective columns 15, 16, with the pair of deflection wheels 17, 18 being arranged in this example at a level above the pair of drive wheels 21, 22. As a result, the pulley 11 is partially encompassed from below by the chain 25 in contrast to the exemplary embodiment shown in FIGS. 1 and 2. Guide shoes 27, 28 are provided which prevent the chain 25 from releasing from the drive wheels 21,22.

Figure 5:
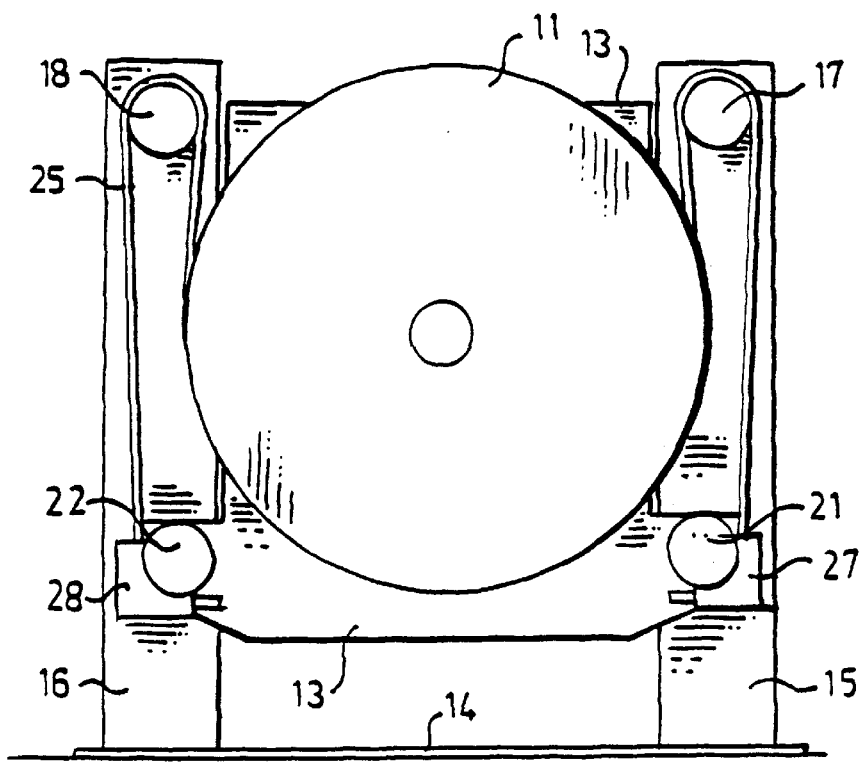
FIG. 5 schematically illustrates a third exemplary embodiment of a lifting and rotating device according to the invention.

FIG. 5 shows that the pair of drive wheels 21, 22 alternatively can be mounted at the carriage 13. In addition, the lifting and rotating device in FIGS. 4 and 5 operates as described in detail in connection with FIGS. 1 and 2.

FIG. 6 shows a lifting and rotating device in accordance with the invention having a relatively simple structure. In this exemplary embodiment, the chain 25 first partially encompasses one drive wheel 22 and thereafter partially encompasses the pulley 11 and finally partially encompasses the second drive wheel 21. No deflection wheels are provided in this exemplary embodiment. The ends of the chain 25 are collected in containers 32, 33. This design of the lifting and rotating device according to the invention also functions as described in connection with FIGS. 1 and 2.

The chain 25 described in connection with the FIGS. 1 to 6 alternatively can be a toothed belt. The ends of the chains or the toothed belt that are shown in FIGS. 2 to 5, are also collected in shaft wells or containers of the type shown in FIG. 6.

The peripheral surface of the pulley 11 needs to exhibit a round (circular) shape only in the area of the arc wherein the chain or the toothed belt is adjacent to the peripheral surface.

A lifting and rotating device according to the invention also can be used with a base that only carries an examination table.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray examination apparatus comprising:

an x-ray imaging component;

a base comprising a fixed part and a carriage mounted to be vertically movable relative to said fixed part, said carriage having a horizontally projecting shaft having a center axis, said x-ray imaging component being rotatably mounted on said shaft for rotation around said center axis and to be vertically movable together with said carriage; and a lifting and rotating device comprising a pulley rotationally mounted at said shaft and having a peripheral surface which is at least partially circular, said pulley being firmly connected to said x-ray imaging component for co-rotation therewith around said center axis, first and second wheels rotationally mounted at said fixed part respectively on opposite sides of said pulley, and a connector entrained around said first and second wheels and at least around said circular portion of said pulley so that when said first and second wheels are respectively simultaneously rotated in different directions said pulley and said x-ray imaging component are vertically moved, and so that when said first and second wheels are simultaneously rotated in a same direction said pulley and said x-ray imaging component rotate around said center axis.

2. An x-ray examination apparatus as claimed in claim 1 comprising third and fourth wheels mounted at said carriage respectively on opposite sides of said pulley, said first and second wheels being disposed at a different height from said third and fourth wheels, and said connector, in succession, partially entraining said first wheel, partially entraining said third wheel, partially entraining said pulley, partially entraining said second wheel and partially entraining said fourth wheel.

3. An x-ray examination apparatus as claimed in claim 2 wherein said first and second wheels are driven wheels.

4. An x-ray examination apparatus as claimed in claim 3 wherein said third and fourth wheels are deflection wheels.

5. An x-ray examination apparatus as claimed in claim 1 comprising third and fourth wheels mounted at said fixed part respectively on opposite sides of said pulley, said first and second wheels being disposed at a different height from said third and fourth wheels, and said connector, in succession, partially entraining said first wheel, partially entraining said third wheel, partially entraining said pulley, partially entraining said second wheel and partially entraining said fourth wheel.

6. An x-ray examination apparatus as claimed in claim 5 wherein said first and second wheels are driven wheels.

7. An x-ray examination apparatus as claimed in claim 5 wherein said third and fourth wheels are deflection wheels.

8. An x-ray examination apparatus as claimed in claim 1 wherein said connector is a chain.

9. An x-ray examination apparatus as claimed in claim 1 wherein said connector is a toothed belt.

10. An x-ray examination apparatus as claimed in claim 1 comprising a duplicate connector connecting said first and second wheels and said pulley identically to said connector, and acting on said pulley in combination with said first and second wheels to rotate and lift said pulley identically to said connector.

* * * * *